(12) United States Patent  
Teeny et al.

(10) Patent No.: US 7,942,883 B2
(45) Date of Patent: May 17, 2011

(54) ACETABULAR SHELL REMOVAL TOOL

(76) Inventors: Steven M. Teeny, Lakewood, WA (US); Steven G. Jacobsen, DuPont, WA (US)

( * ) Notice: Subject to any disclaimer, the term of this patent is extended or adjusted under 35 U.S.C. 154(b) by 0 days.

(21) Appl. No.: 12/820,963

(22) Filed: Jun. 22, 2010

(65) Prior Publication Data

US 2010/0262155 A1    Oct. 14, 2010

Related U.S. Application Data

(62) Division of application No. 11/046,546, filed on Jan. 28, 2005, now Pat. No. 7,744,602.

(51) Int. Cl.
A61B 17/92    (2006.01)
(52) U.S. Cl. ......................................................... 606/99
(58) Field of Classification Search ................ 606/1, 53, 606/86 R, 91, 99, 100; 623/22.15, 22.18, 623/22.21–22.39
See application file for complete search history.

(56) References Cited

U.S. PATENT DOCUMENTS

| 3,147,749 | A | 9/1964 | Marsh |
|---|---|---|---|
| 3,677,593 | A | 7/1972 | Wahlberg |
| 4,712,951 | A | 12/1987 | Brown |
| 4,716,894 | A | 1/1988 | Lazzeri et al. |
| 5,112,338 | A | 5/1992 | Anspach |
| 5,325,630 | A | 7/1994 | Allenbaugh |
| 5,431,657 | A | 7/1995 | Rohr |
| 5,540,697 | A | 7/1996 | Rehmann et al. |
| 5,584,837 | A | 12/1996 | Petersen |
| 5,830,215 | A | 11/1998 | Incavo |
| 5,938,701 | A | 8/1999 | Hiernard et al. |
| 5,954,727 | A | 9/1999 | Collazo |
| 5,976,148 | A | 11/1999 | Charpenet et al. |
| 6,013,082 | A | 1/2000 | Hiernard et al. |
| 6,022,357 | A | 2/2000 | Reu et al. |
| 6,053,877 | A | 4/2000 | Banik et al. |
| 6,132,469 | A | 10/2000 | Schroeder |
| 6,152,930 | A | 11/2000 | Mastrorio |
| 6,395,005 | B1 | 5/2002 | Lovell |
| 6,565,575 | B2 | 5/2003 | Lewis |
| 2002/0116007 | A1 | 8/2002 | Lewis |
| 2003/0212402 | A1 | 11/2003 | White et al. |
| 2004/0073224 | A1 | 4/2004 | Bauer |
| 2004/0133210 | A1 | 7/2004 | Wolford |
| 2004/0167528 | A1 | 8/2004 | Schantz |
| 2006/0195105 | A1 | 8/2006 | Teeny |
| 2006/0200165 | A1 | 9/2006 | Tulkis |
| 2008/0249531 | A1 | 10/2008 | Patterson |
| 2009/0267360 | A1 | 10/2009 | Anderson et al. |

*Primary Examiner* — Eduardo C Robert
*Assistant Examiner* — Christian Sevilla
(74) *Attorney, Agent, or Firm* — Chernoff Vilhauer LLP

(57) ABSTRACT

A tool for separating an acetabular shell of a hip prosthesis from the surrounding pelvic bone includes a fixture which attaches to the acetabular shell and has a chisel guide mounted on it. A chisel associated with the chisel guide is curved to conform to the outer periphery of the acetabular shell, and the chisel guide causes the chisel to circumscribe the acetabular shell as the chisel is inserted between the acetabular shell and the pelvis.

10 Claims, 10 Drawing Sheets

ACETABULAR SHELL REMOVAL TOOL

BACKGROUND OF THE INVENTION

Total hip anthroplasty has become a relatively common procedure. It also is becoming more common to replace the prosthesis after a period of time. A difficulty in doing this is that the acetabular shell of the prosthesis will become completely embedded in the surrounding bone and needs to be cut free. The traditional method of accomplishing this has been to use hand-held, curved chisels and a mallet to cut and pry the acetabular shell away from the bone. A problem with this process is that it is difficult to keep the chisel precisely at the periphery of the acetabular shell and often excess bone is removed with the shell.

The X-PLANT acetabular shell removal tool sold by the Zimmer Company reduces this problem to some degree. The X-PLANT removal tool provides a curved chisel having the same contour as the outer periphery of the acetabular shell. The chisel is attached to a shaft having a ball at its extremity which is sized to be inserted into the socket in the polyethylene liner which is located in the acetabular shell to receive the femural head of the prosthesis. As the tool is manipulated and struck with a mallet to break the acetabular shell free from the surrounding bone, the ball pivots in the socket and keeps the chisel blade close to the periphery of the acetabular shell.

While the X-PLANT tool is an improvement over the traditional hand-held chisels, it does have one significant shortcoming. Often the acetabular shell is attached to the pelvis with screws which extend through the shell and into the surrounding bone. These screws need to be removed before the shell can be removed and doing this requires that the polyethylene liner be removed from the shell, which often damages the mechanism which holds the liner in place. As a result the liner moves when the X-PLANT tool is used which prevents the tool from cutting as close to the periphery of the shell as it otherwise would.

The subject invention overcomes the foregoing shortcomings of the prior art tools for removing the acetabular shell by providing a fixture which attaches to the shell. The fixture has a chisel guide mounted on it. The chisel guide causes a chisel to move along a path such that it substantially circumscribes the outer surface of the shell when the chisel is moved.

A BRIEF DESCRIPTION OF THE DRAWINGS

The foregoing and other objectives, features, and advantages of the invention will be more readily understood upon consideration of the following detailed description of the invention taken in conjunction with the accompanying drawings.

DETAILED DESCRIPTION OF PREFERRED EMBODIMENTS

Figure 1:
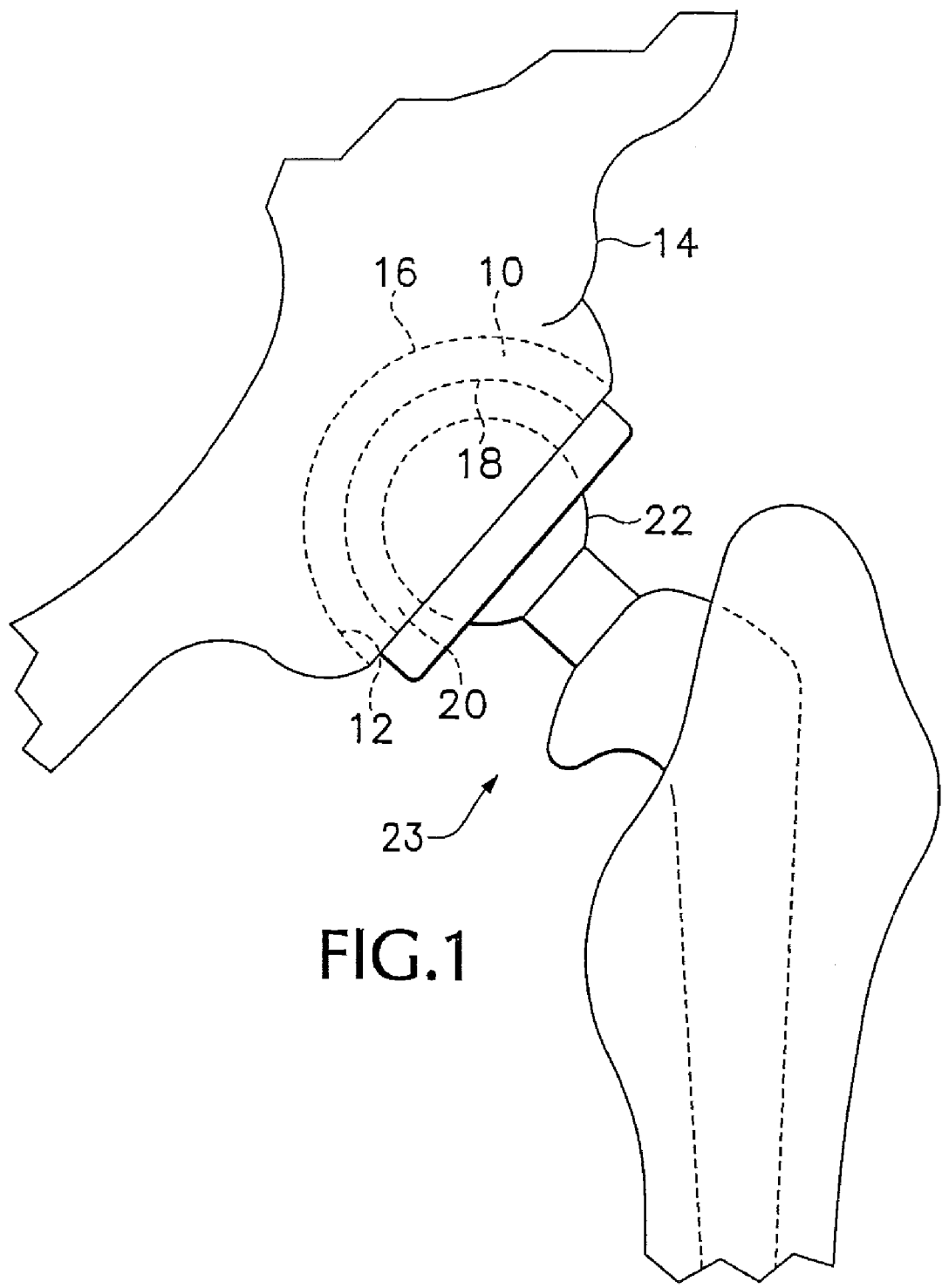
FIG. 1 is a side elevation view showing a hip prosthesis.
Figure 2:
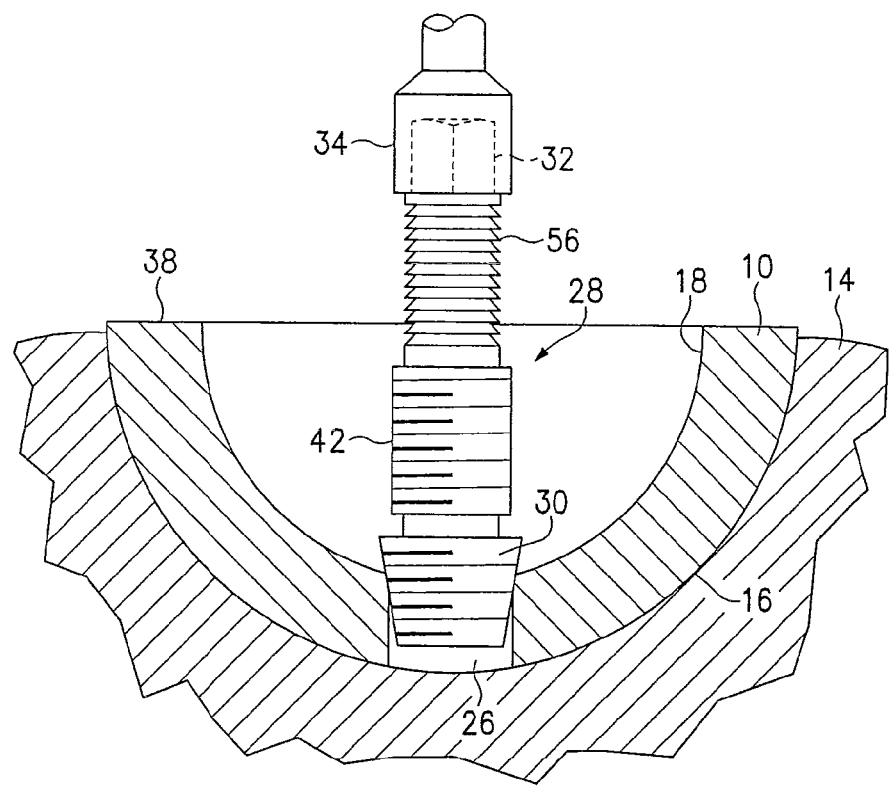
FIGS. 2-7 are side elevation views, at various stages of completeness, showing an acetabular shell removal tool embodying the subject invention.

Referring to FIG. 1 of the drawings, a total hip anthroplasty includes placing an acetabular shell 10 in a mating recess 12 in the pelvis 14. The shell 10 is typically stainless steel, has a semi-spheriodal outer surface 16 which contacts the pelvis and a semi-spheriodal inner surface 18 which is spaced inwardly from the outer surface. Located in the shell is a polyethylene liner 20 having a cavity which carries the femural head 22 at the extremity of the femural component 23 of the prosthesis. The liner is locked in place in the shell by a locking mechanism, not shown. With time the pelvis bone becomes firmly joined to the shell 10. As a result, when it becomes necessary to remove the shell, the bone must be broken or cut away from the shell.

The tool of the subject invention facilitates the removal of the shell. Referring to FIGS. 2-9 of the drawings, a first embodiment of the tool 24 is utilized where the shell has an opening 26 at its center which was used to instill the shell. The tool 24 includes an anchor 28, FIG. 2, which attaches to the shell. Located at the inner end of the anchor 28 is a seat 30. The seat 30 can either have self-tapping threads or threads that mate with the existing threads in the opening 26. A hex head 32 is located at the outer end of the anchor so that a wrench 34 can be attached to the anchor to screw the seat 30 into the opening 26.

Figure 3:
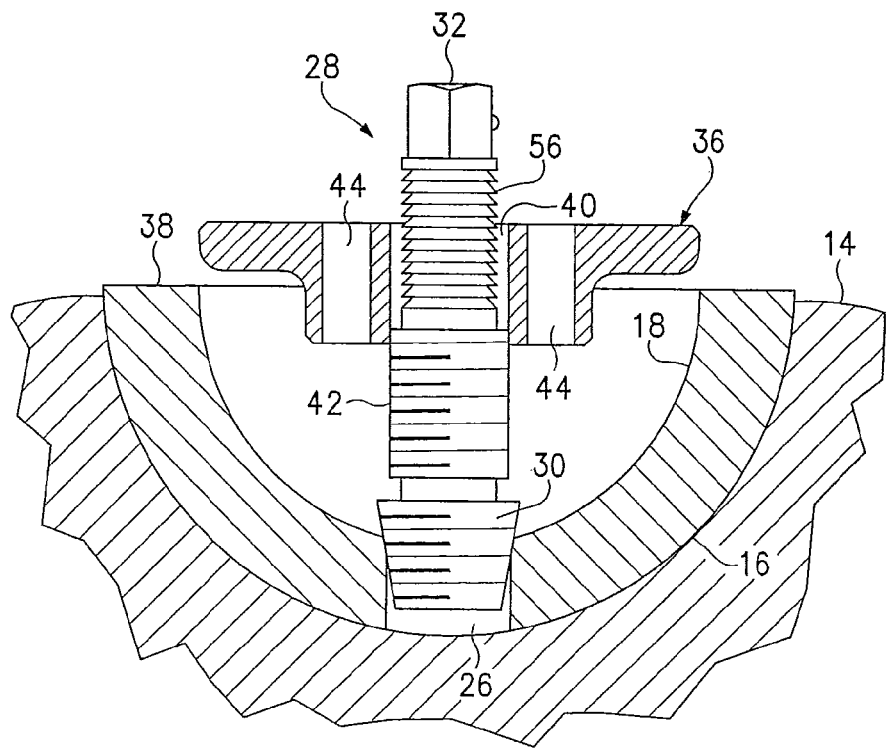
Figure 4:
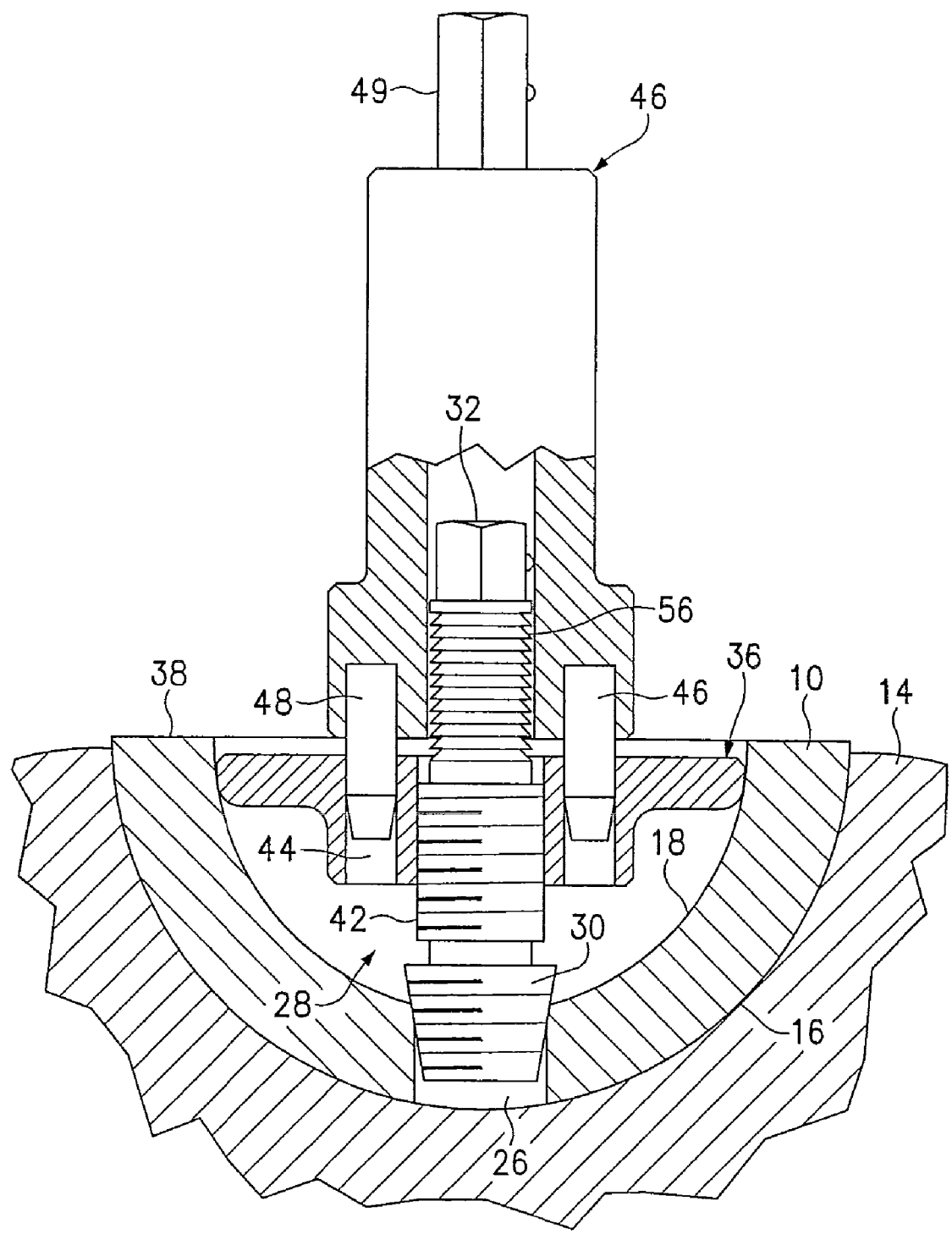

Referring now also to FIGS. 3 and 4, once the anchor is in place a centering plate 36 is installed on it. The centering plate 36 is circular in cross-section and has a diameter which causes it to contact the inner surface 18 of the shell slightly below its outer edge 38. Located in the center of the centering plate 36 is a hole 40. The hole 40 and the center portion 42 of the anchor have mating threads. Thus, as the centering plate is screwed onto the anchor it causes the anchor to become centered in the shell and be perpendicular to the outer edge 38 of the shell. The centering plate 36 has a series of holes 44 located in it and a wrench 46, having pins 48 which engage the holes, fits over the anchor to facilitate screwing the centering plate tightly into the shell. A hex head 49 is placed at the top of the wrench 44 for this purpose.

Figure 5:
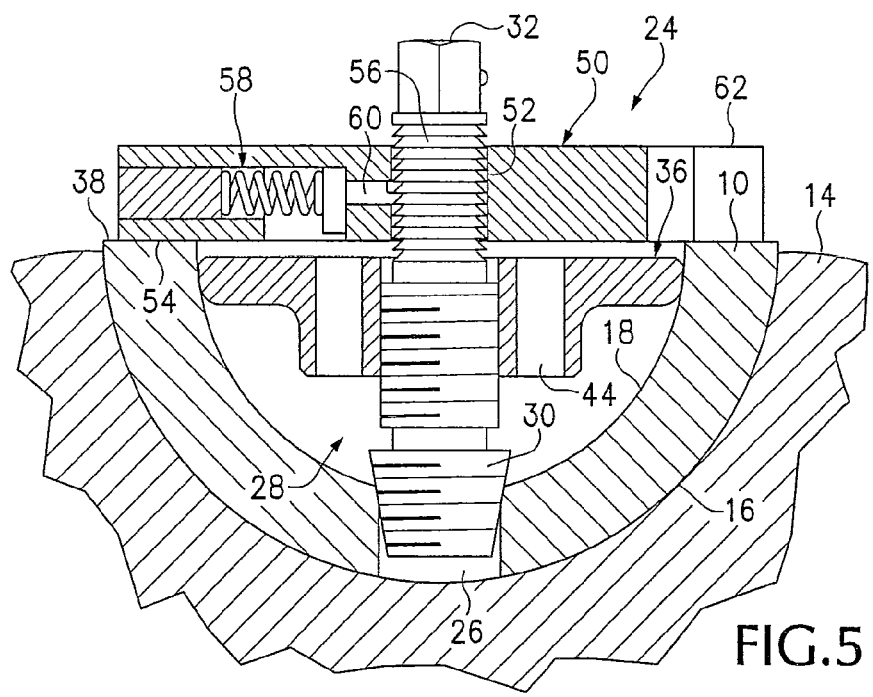

Referring now to FIG. 5, a cylindrical locking plate 50 is placed on the anchor outwardly of the centering plate 36. The locking plate has a central hole 52 having an inner diameter which is larger than the outer diameter of the anchor 28. The locking plate is large enough that the periphery of its base 54 rests on the edge 38 of the shell 10. The portion of the anchor which fits through the hole 52 in the centering plate has a series of saw-tooth-shaped rings 56 formed in its outer surface. Located in the locking plate 50 are three spring-loaded detents 58 having chisel-shaped teeth 60 which engage the saw-tooth rings 56 in the anchor, FIG. 8. The detents center the locking plate on the anchor and hold it tightly in place against the outer edge 38.

Figure 6:
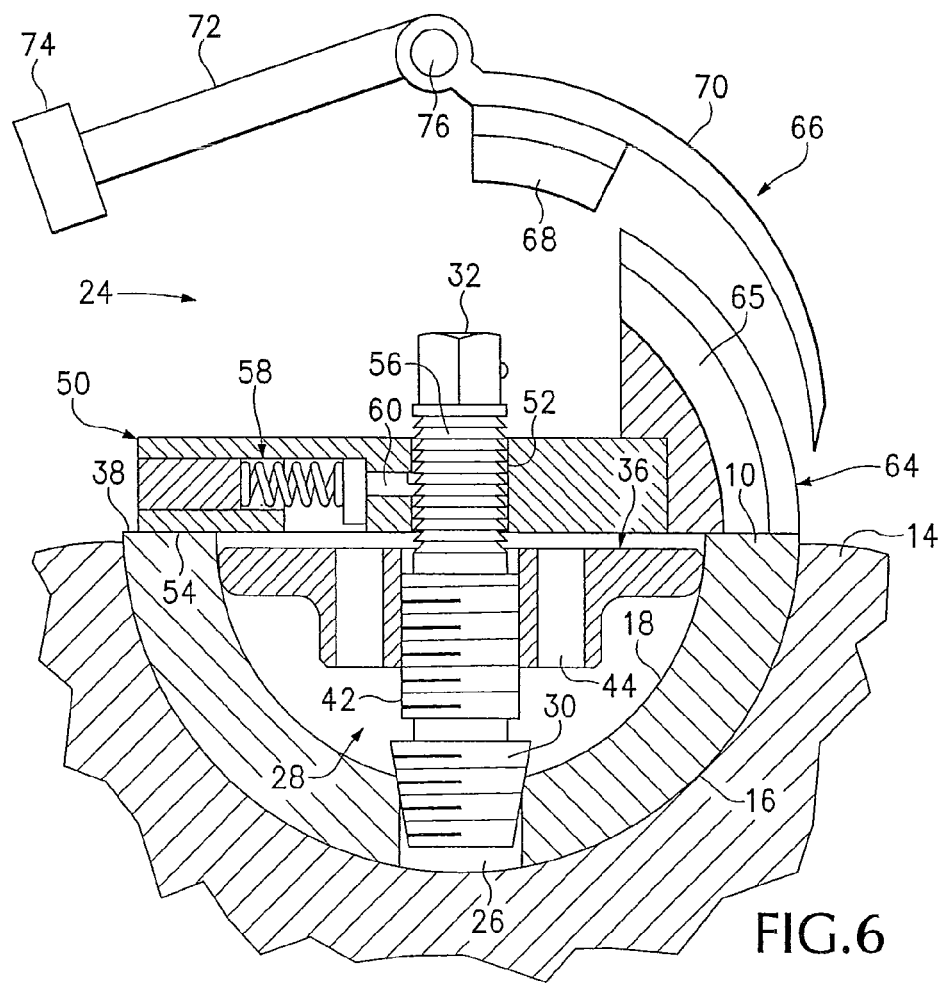
Figure 8:
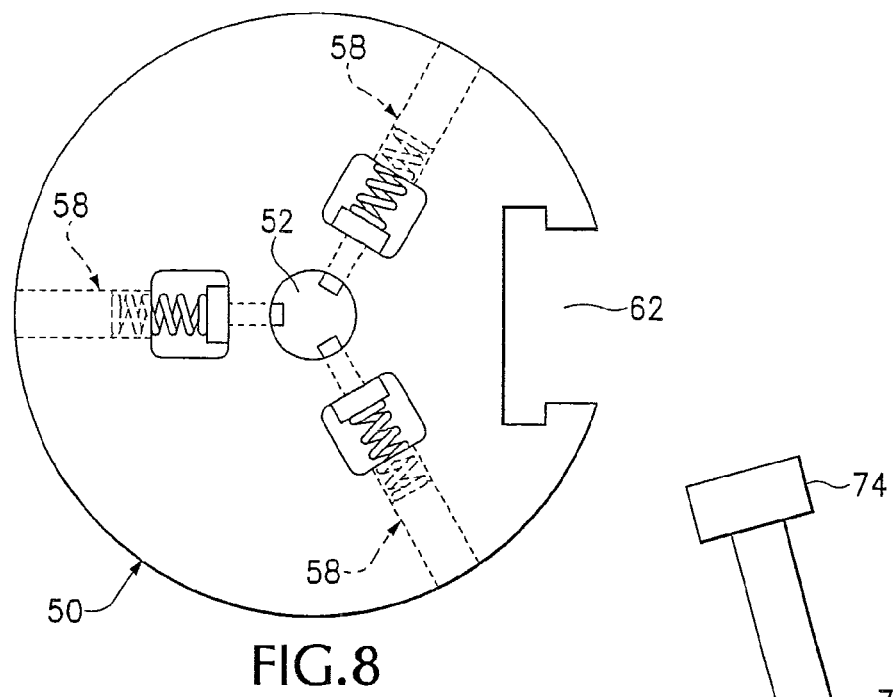
FIG. 8 is a bottom view of a locking plate which is an element of the tool.
Figure 7:
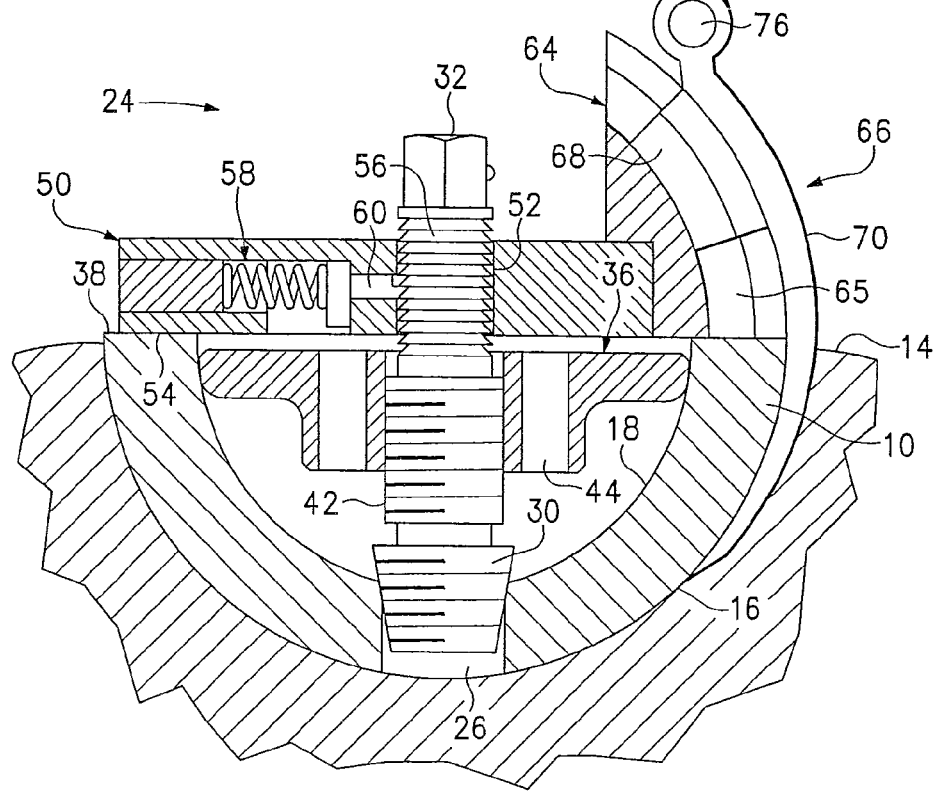
Figure 9:
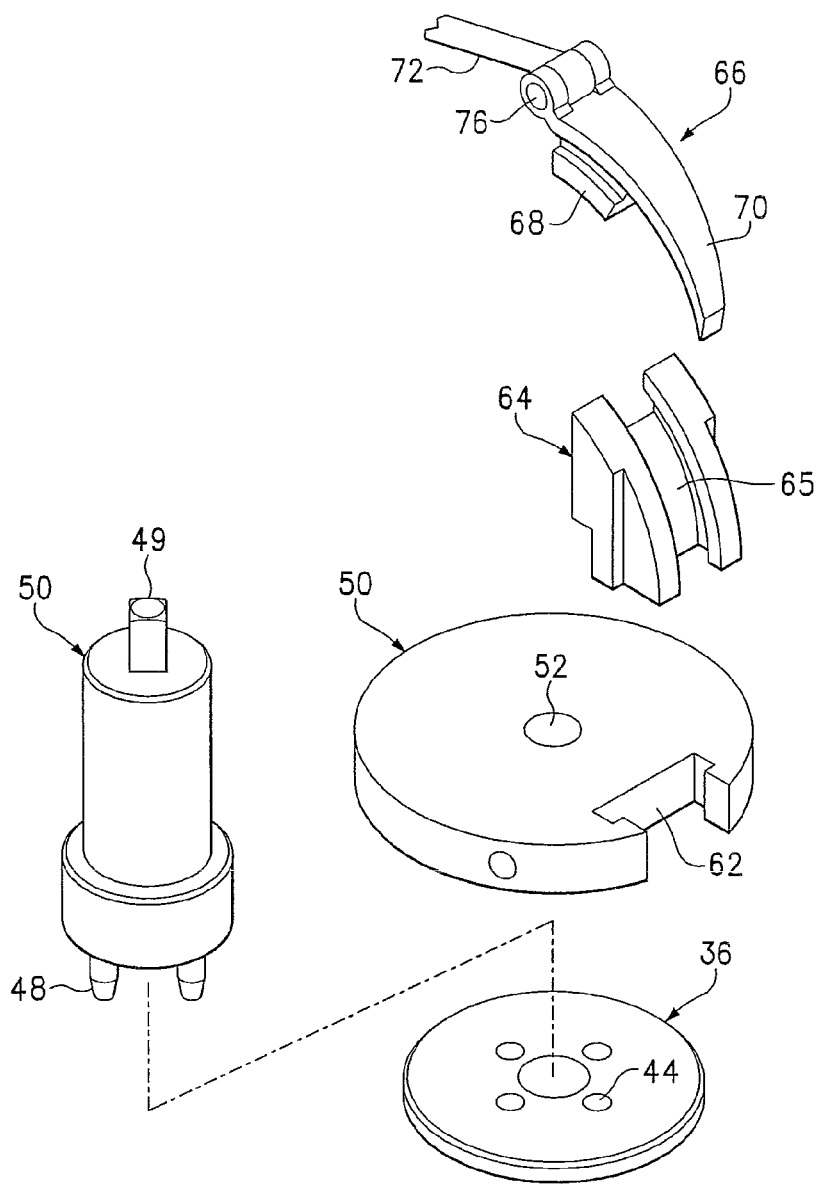
FIG. 9 is an exploded view showing the various parts of the tool.

Located in the locking plate 50 is a T-shaped slot 62 which receives a chisel guide 64, FIG. 6. Located in the chisel guide is a track 65, which in the embodiment illustrated in FIGS. 2-9 has the same curvature as the outer surface 16 of the shell. A chisel 66 has a rail 68 attached to it which fits slidably in the track 65 in the chisel guide. The chisel has a curved blade 70 which also has the same curvature as the outer surface 16 of the shell. The blade 70 is wider at its base than it is at its tip as can be seen in FIG. 8. The chisel guide and chisel are configured such that when the chisel is moved in the chisel guide toward the pelvis it closely circumscribes the outer surface 16 of the shell, FIG. 7. As will be described more fully below, the chisel does not necessarily move in the chisel guide. The chisel guide and chisel can move together as a unit.

Attached to the base of the chisel is a rod 72 having an impact pad 74 located at its extremity. The rod is attached to the chisel through a hinge 76. The impact pad 74 can be struck with a mallet to drive the chisel 66 inwardly between the shell 10 and pelvic bone 14 when the rod is in the position shown in FIG. 7. Alternatively, the rod can be rotated 180 degrees so that when the impact pad 74 is struck with a mallet the chisel is driven in the opposite direction. As will be more fully explained below, the impact pad can be connected to the chisel through a non-rotating element also. The entire tool 24 is shown exploded in FIG. 9.

Figure 13:
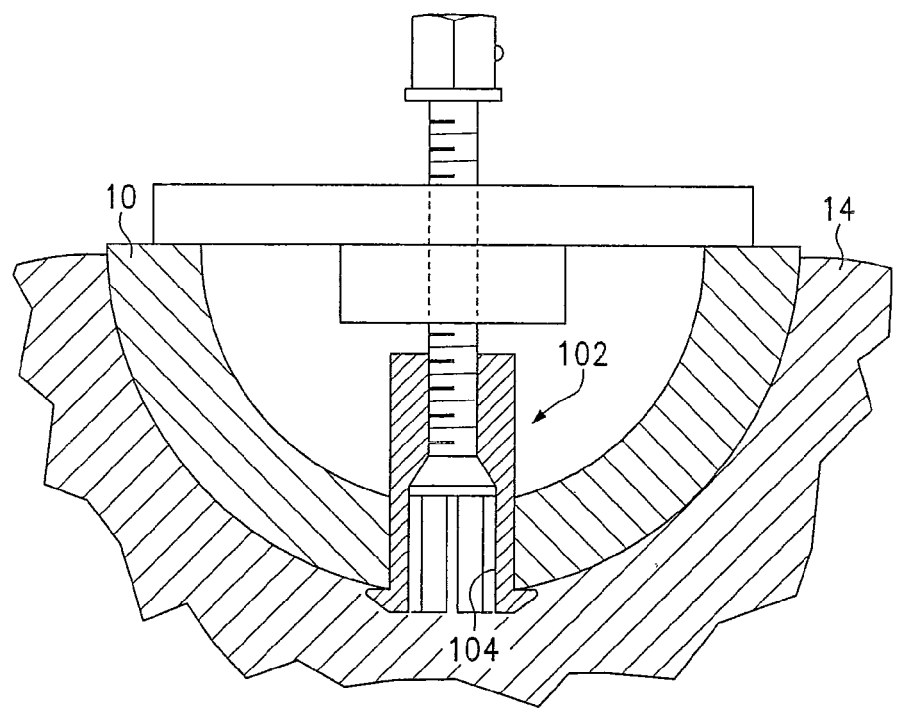
FIG. 13 is a side elevation view of another embodiment of the tool.

An alternative apparatus for attaching the anchor to the shell is shown in FIG. 13. In this embodiment the anchor 102 has a spring-loaded expandable mandrel 104 which fits in the opening 26 in the center of the shell 10. A locking mechanism, not shown, locks the mandrel in its expanded position once it is installed.

Figure 10:
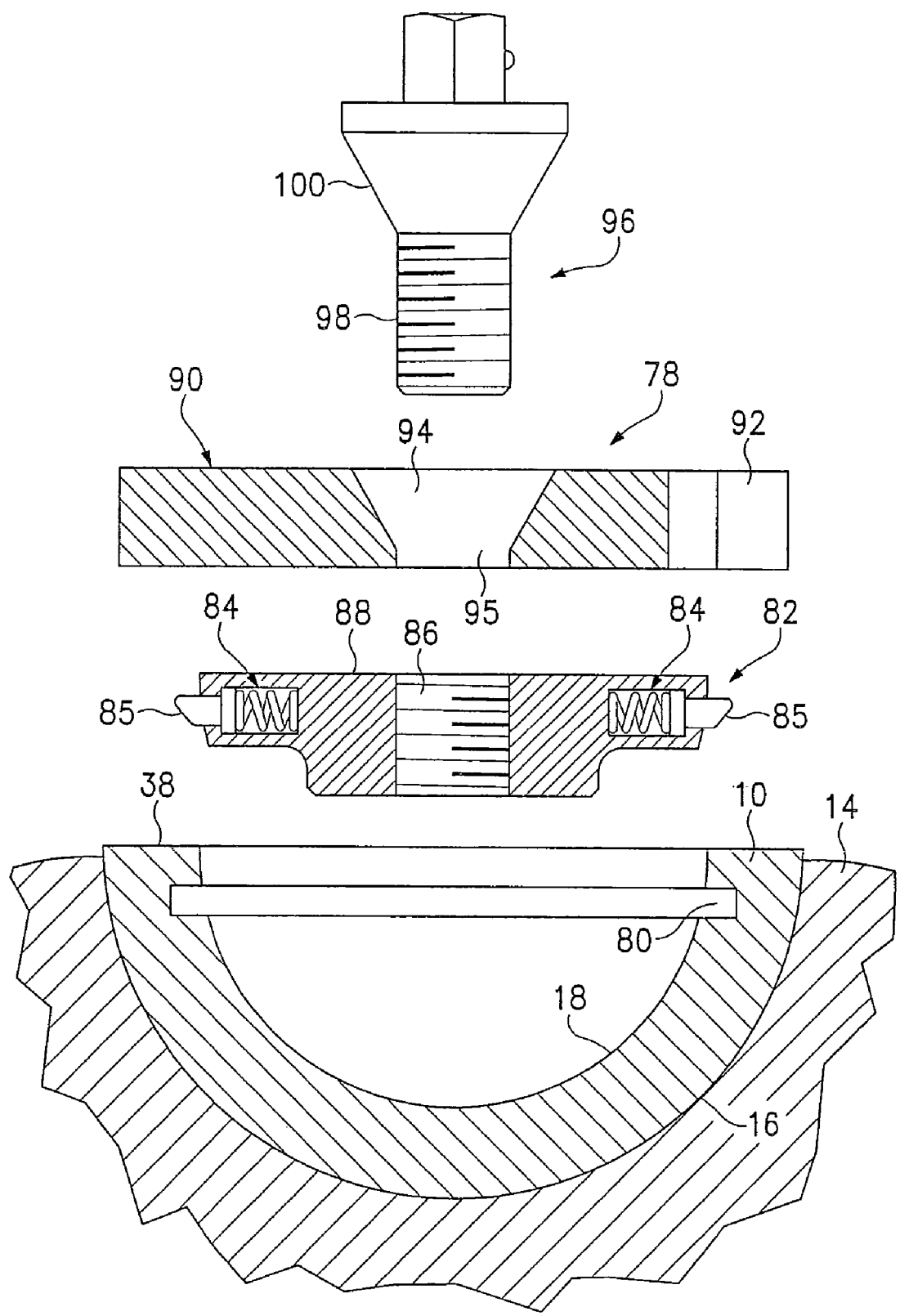
FIGS. 10-12 are side elevation views of another embodiment of the tool in various stages of completeness.
Figure 11:
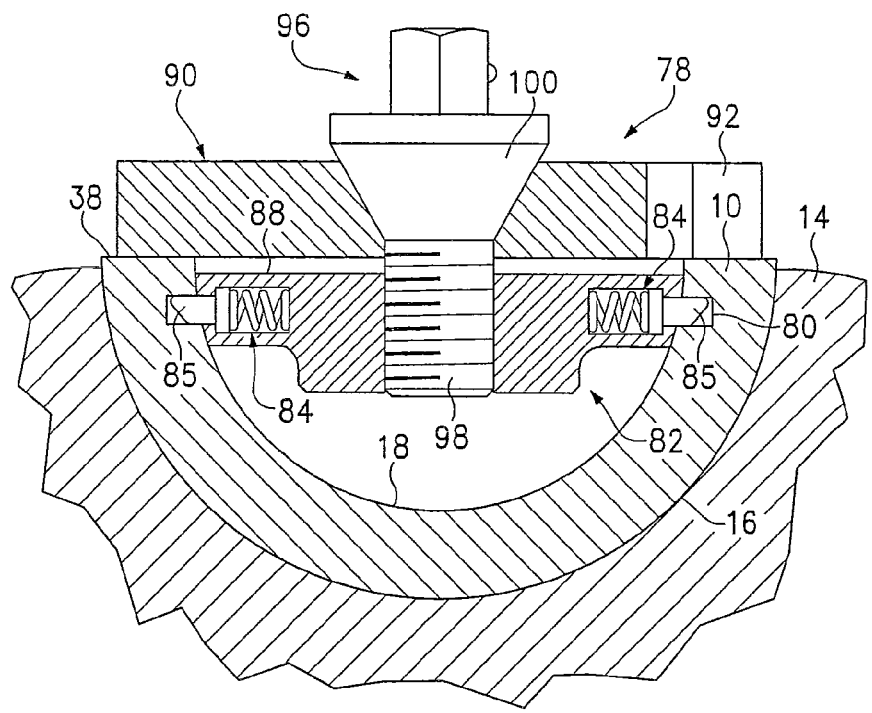
Figure 12:
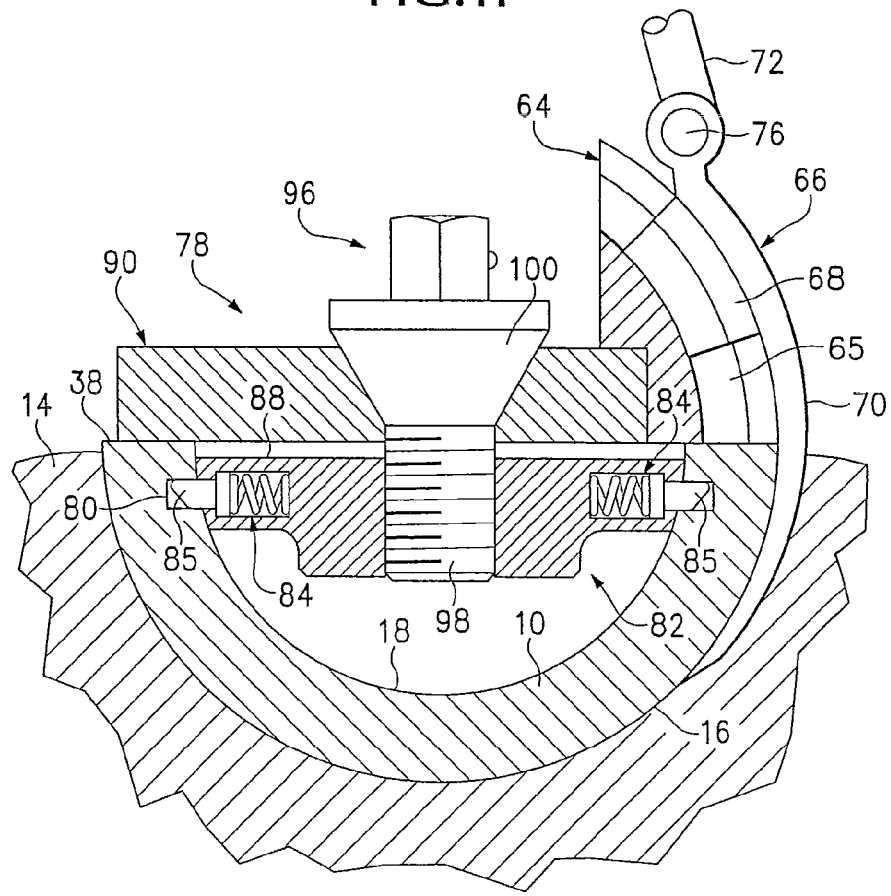

Referring now to FIGS. 10-12, when the acetabular shell 10 does not have an opening in it, a second embodiment of the tool 78 is used. In this embodiment the tool is attached to the shell 10 through a circumferential groove or annular slot 80 which is located in the upper portion of the inner surface 18 of the shell to hold the polyethylene liner 20 into the shell. The tool 78 includes a fixture, the fixture comprising a centering plate or clamping ring 82 having an outer diameter which is slightly less than the diameter of the inner surface of the shell at the location of the slot 80. The clamping ring 82 has three spring-loaded detents 84 having teeth 85 that project from the periphery of the clamping ring and snap into the slot 80 when the clamping ring is pushed into the shell. The detents 84 are similar to the detents 58. The clamping ring has a planer top surface 88 which is located below the upper edge 38 of the shell when the clamping ring 82 is inserted into the shell and the teeth 85 are seated in the slot 80. Located in the center of the clamping ring 82 is a threaded hole 86.

Attached to the clamping ring 82 is a locking plate or plate 90 which has a T-shaped slot 92 that is similar to the slot 62 and receives the chisel guide 64. The chisel guide 64 includes an arcuate track 65. The chisel 66 has a rail 68 attached to it which interfits with the track 65. The chisel 66 includes an impact pad, configured similarly as impact pad 74 in FIG. 7. An opening 95 having an inwardly conical-shaped upper portion 94 extends through the plate 90. A bolt 96 has a threaded cylindrical lower portion 98 that mates with the threaded opening 86 in the plate 90. The upper portion 100 of the bolt 96 is conical and mates with the conical portion 94 of the opening 95. Thus, when the bolt 96 is inserted through the opening 95 in the plate 90 and into the threaded hole 86 and tightened, the plate is centered on the clamp ring and pulled tight against the upper edge 38 of the shell, FIG. 11. The chisel 66 is then inserted in the chisel guide 64 and is operated in the same manner that it is with the first embodiment of the tool, FIG. 12.

Figure 14:
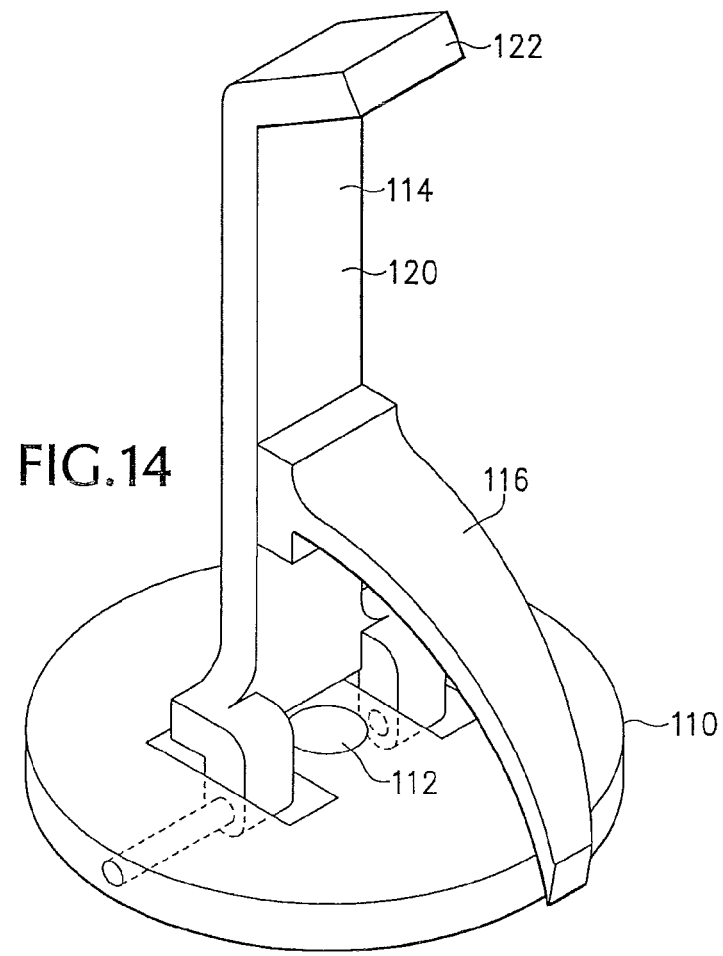
FIG. 14 is a perspective view of yet another embodiment of the tool.
Figure 15:
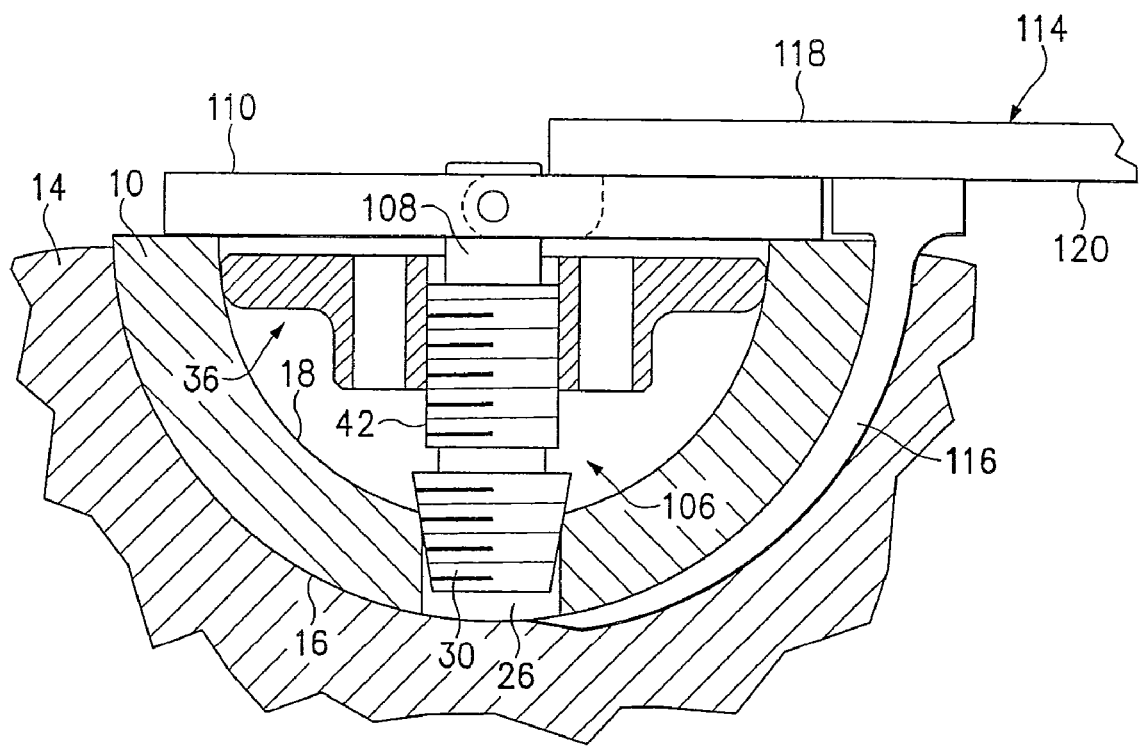
FIG. 15 is a side elevation view of the tool of FIG. 14 installed on an acetabular shell.

A third embodiment of the invention is shown in FIGS. 14 and 15. In this embodiment the anchor 106 is similar to the anchor 28 in the first embodiment except that the portion having the saw-tooth rings is replaced by a cylindrical pin 108 which extends slightly outwardly from the shell 10. A cylindrical mounting plate 110 rests on the upper edge 38 of the shell 10 and has a central hole 112 which receives the pin 108. Thus, the mounting plate is freely rotatable about the pin 108. An elongate chisel guide 114, which is mounted on the mounting plate 110, rotates between a retracted position, FIG. 14, where its longitudinal axis is perpendicular to the plane of the mounting plate, and an inserted position, FIG. 15, where its elongate axis is substantially parallel with the plane of the mounting plate. Rigidly attached to the chisel guide is a chisel 116 which has substantially the same shape as the chisel 66. When the chisel guide 114 is rotated to the inserted position the chisel substantially circumscribes the shell 10.

With this embodiment the chisel guide also acts as an impact pad. Striking the chisel guide on the outer side 118 pushes the chisel 116 inwardly between the shell 10 and the pelvic bone 14, and striking the chisel guide on the inner side 120 pulls the chisel back out. In addition, a lever 122 located at the top of the chisel guide allows the mounting plate to be rotated as the chisel is being pushed inwardly so that the chisel does not have to continuously be pulled back, relocated and pushed in again.

The terms and expressions which have been employed in the forgoing specification are used therein as terms of description and not of limitation, and there is no intention in the use of such terms and expressions of excluding equivalence of the features shown and described or portions thereof, it being recognized that the scope of the invention is defined and limited only by the claims which follow.

We claim:

1. A tool for removing the acetabular shell of an artificial hip, having a semi-spheroidal outer surface and a semi-spheroidal inner surface, said tool comprising:
   (a) a fixture which attaches to the acetabular shell;
   (b) a chisel guide mounted on said fixture;
   (c) a chisel associated with said chisel guide, wherein said chisel guide controls the movement of said chisel such that said chisel substantially circumscribes the outer surface of the acetabular shell when moved;
   (d) wherein said chisel is slidably carried by said chisel guide; and
   (e) wherein the shell has a circumferential groove located on its inner surface and said fixture includes a centering plate which is circular in cross-section and fits into the shell and has one or more detents which engage said groove to attach said centering plate to the shell.

2. The tool of claim 1 including an anchor which attaches centrally to said centering plate and extends outwardly from the shell.

3. The tool of claim 2 wherein the shell has a radially extending edge and said fixture includes a cylindrical locking plate having a central opening which allows said locking plate to be placed on said anchor, and a peripheral base which rests on the said edge of the shell.

4. The tool of claim 3 wherein said locking plate includes a locking mechanism which holds said locking plate on said anchor when said peripheral base is resting on said edge of the shell.

5. The tool of claim 3 wherein said chisel guide releasably attaches to said locking plate.

6. The tool of claim 5 wherein said chisel guide includes an arcuate track.

7. The tool of claim 6 wherein said chisel has a rail which interfits with said track in said chisel guide.

8. The tool of claim 7 wherein said chisel is arcuate along a longitudinal axis and has an inner surface which is the same shape as the outer surface of said acetabular shell.

9. The tool of claim 8 wherein said inner surface is arcuate along a transverse axis and has a radius which is equal to the radius of the outer surface of the shell.

10. The tool of claim 9 wherein said chisel includes an impact pad which allows said chisel to be moved in either direction by selectively striking the impact pad with a mallet.

\* \* \* \* \*